(12) United States Patent
Miller

(10) Patent No.: US 8,211,065 B2
(45) Date of Patent: Jul. 3, 2012

(54) ENVELOPING NEEDLE STICK PROTECTION DEVICE

(76) Inventor: Stuart H. Miller, Clifton, NJ (US)

(*) Notice: Subject to any disclaimer, the term of this patent is extended or adjusted under 35 U.S.C. 154(b) by 224 days.

(21) Appl. No.: 12/784,967

(22) Filed: May 21, 2010

(65) Prior Publication Data

US 2011/0288490 A1    Nov. 24, 2011

(51) Int. Cl.
*A61M 5/32* (2006.01)
(52) U.S. Cl. ........................................ 604/198
(58) Field of Classification Search ............. 604/198
See application file for complete search history.

(56) References Cited

U.S. PATENT DOCUMENTS

| | | | |
|---|---|---|---|
| 4,813,940 A | 3/1989 | Parry | |
| 4,998,924 A * | 3/1991 | Ranford | 604/198 |
| 5,106,379 A | 4/1992 | Leap | |
| 5,279,566 A * | 1/1994 | Kline et al. | 604/110 |
| 5,472,430 A | 12/1995 | Vaillancourt et al. | |
| 5,591,138 A | 1/1997 | Vaillancourt | |
| 5,795,336 A | 8/1998 | Romano et al. | |
| 5,984,899 A | 11/1999 | D'Alessio et al. | |
| 6,183,445 B1 | 2/2001 | Lund et al. | |
| 6,322,540 B1 | 11/2001 | Grabis et al. | |
| 6,325,781 B1 | 12/2001 | Takagi et al. | |
| 6,344,032 B1 | 2/2002 | Perez et al. | |
| 6,969,376 B2 | 11/2005 | Takagi et al. | |
| 7,211,065 B2 | 5/2007 | Miller | |
| 7,727,190 B2 | 6/2010 | Miller | |
| 2003/0144630 A1 | 7/2003 | Chang et al. | |
| 2008/0215001 A1 * | 9/2008 | Cowe | 604/110 |
| 2010/0042053 A1 * | 2/2010 | Dillard, III | 604/198 |

* cited by examiner

*Primary Examiner* — Nicholas Lucchesi
*Assistant Examiner* — Jason Flick
(74) *Attorney, Agent, or Firm* — Welsh Flaxman & Gitler LLC

(57) ABSTRACT

A needle stick protection device includes a housing shaped and dimensioned for positioning about a syringe including a needle extending therefrom. The housing includes a first housing member telescopically coupled to a second housing member. The first housing member includes a first end shaped and dimensioned for receiving the syringe and a second end. The second housing member includes a first end and a substantially closed second end. The second end includes an aperture shaped and dimensioned to permit the passage of the needle therethrough. A locking assembly is associated with the first housing member and the second housing member for selectively controlling movement of the first housing member relative to the second housing member.

12 Claims, 5 Drawing Sheets

ENVELOPING NEEDLE STICK PROTECTION DEVICE

BACKGROUND OF THE INVENTION

1. Field of the Invention

The invention relates to a device for preventing needle sticks. More particularly, the invention relates to a device for preventing needle sticks wherein the needle is selectively locked and released relative to a shielding device, and may ultimately be permanently locked once it is ready for disposal.

2. Description of the Prior Art

As those within the medical field have developed an understanding that a variety of diseases may be transferred via unclean and previously used needles, many devices have been developed for protecting medical practitioners and other individuals from previously used needles. Many currently available needle stick protection devices operate by either withdrawing the used needle into a hard protective shell or extending a hard protective shell over the used needle. These devices are generally utilized once and are then discarded in an approved collection device.

While most procedures permit the disposal of needles after a single usage, some medical procedures require that needles be used more than once during a procedure on a patient. However, these used needles may be passed between physicians and other medical practitioners several times during the procedure. As such, a possibility exists that physicians and other medical practitioners may be stuck with these used needles during the procedure.

A need, therefore, exists for a needle stick protection device in which the needle is selectively shielded and unshielded as the medical procedure dictates, and ultimately permanently locked in a shielded orientation once it is ready for disposal. The present invention provides such a needle stick protection device.

SUMMARY OF THE INVENTION

It is, therefore, an object of the present invention to provide a needle stick protection device including a housing shaped and dimensioned for positioning about a syringe including a needle extending therefrom. The housing includes a first housing member telescopically coupled to a second housing member. The first housing member includes a first end shaped and dimensioned for receiving the syringe and a second end. The second housing member includes a first end and a substantially closed second end. The second end includes an aperture shaped and dimensioned to permit the passage of the needle therethrough. A locking assembly is associated with the first housing member and the second housing member for selectively controlling movement of the first housing member relative to the second housing member. The locking assembly includes a resilient first arcuate member and a resilient second arcuate member coupled at opposite ends thereof to define a locking ring shaped and dimensioned for positioning about the first housing member. The first arcuate member includes a concave inner surface. The second arcuate member includes a concave inner surface from which an inwardly directed long locator plug. The locking ring moves between a locked orientation with the inwardly directed long locator plug preventing relative movement between the first housing member and the second housing member and a release orientation with the inwardly directed long locator plug moved from its interference position preventing relative movement between the first housing member and the second housing member.

It is also an object of the present invention to provide a needle stick protection device wherein the first arcuate member covers an arc of less than 180 degrees and the second arcuate member covers an arc of more than 180 degrees.

It is another object of the present invention to provide a needle stick protection device wherein the concave inner surface of the first arcuate member has a resting radius of curvature which is less than a resting radius of curvature of the concave inner surface of the second arcuate member.

It is a further object of the present invention to provide a needle stick protection device wherein a radius of curvature along a convex outer surface of the first housing member is substantially the same as the resting radius of the curvature along the concave inner surface of the second arcuate member.

It is also an object of the present invention to provide a needle stick protection device wherein the locking ring is biased to a resting orientation with the concave inner surface of the second arcuate member conforming to the convex outer surface of the first housing member and the concave inner surface of the first arcuate member spaced from the convex outer surface of the first housing member.

It is another object of the present invention to provide a needle stick protection device wherein the concave inner surface of the first arcuate member has a resting radius of curvature which is less than a resting radius of curvature of the concave inner surface of the second arcuate member.

It is a further object of the present invention to provide a needle stick protection device wherein a radius of curvature along a convex outer surface of the first housing member is substantially the same as the resting radius of the curvature along the concave inner surface of the second arcuate member.

It is also an object of the present invention to provide a needle stick protection device wherein the locking ring is biased to a resting orientation with the concave inner surface of the second arcuate member conforming to the convex outer surface of the first housing member and the concave inner surface of the first arcuate member spaced from the convex outer surface of the first housing member, however, when one presses with sufficient pressure upon the first arcuate member and forces the concave inner surface of the first arcuate member toward the convex outer surface of the first housing member, the bias generated by the interaction between the first arcuate member, the second arcuate member and the convex outer surface of the first housing member is overcome and the locking ring is moved to its release orientation.

It is another object of the present invention to provide a needle stick protection device wherein the resting orientation is a locked orientation and wherein the inwardly directed long locator plug extends through a wall of the first housing member for engagement with the second housing member.

It is a further object of the present invention to provide a needle stick protection device wherein the first arcuate member includes an inwardly directed short locator plug extending from the concave inner surface of the first arcuate member and the inwardly directed short locator plug is spaced from the wall of the first housing member when the locking ring is in its locked orientation.

It is also an object of the present invention to provide a needle stick protection device wherein the locking ring, when in its release orientation, has the concave inner surface of the first arcuate member bent to substantially conform to the convex outer surface of the first housing member with the inwardly directed short locator plug seated within a short plug aperture formed in the wall of the first housing member but not extending through the wall of the first housing member, and the concave inner surface of the second arcuate member is moved from the convex outer surface of the first housing member, and the inwardly directed long locator plug is moved radially outwardly such that it moves from its interference position extending through the long plug aperture in the first housing member and a retracted recess or a covered recess of the second housing member.

It is another object of the present invention to provide a needle stick protection device wherein the locking ring, when in its release orientation, has the concave inner surface of the first arcuate member bent to substantially conform to the convex outer surface of the first housing member, and the concave inner surface of the second arcuate member is moved from the convex outer surface of the first housing member, and the inwardly directed long locator plug is moved radially outwardly such that it moves from its interference position extending through the long plug aperture in the first housing member and a retracted recess or a covered recess of the second housing member.

Other objects and advantages of the present invention will become apparent from the following detailed description when viewed in conjunction with the accompanying drawings, which set forth certain embodiments of the invention.

DESCRIPTION OF THE PREFERRED EMBODIMENT

Figure 1:
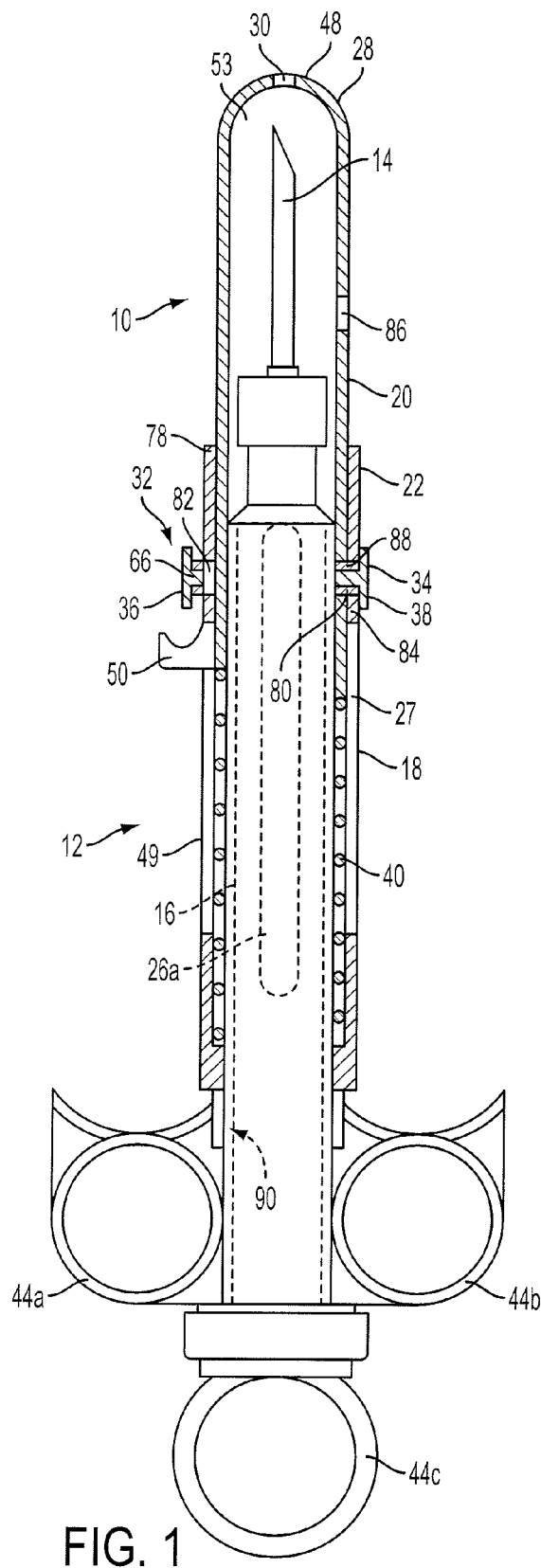
FIG. 1 is a side partial cross-sectional view of the present needle stick protection device in its covered orientation.
Figure 2:
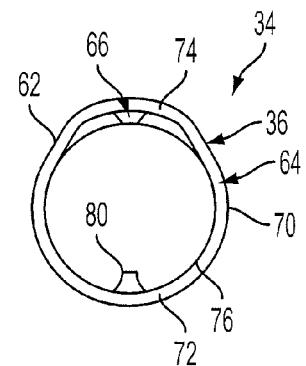
FIG. 2 is a side view of the shield trigger.
Figure 3:
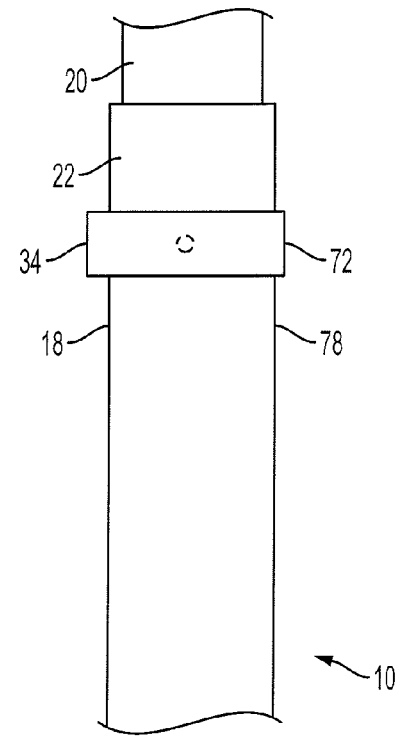
FIG. 3 is a detailed side plan view showing the shield trigger on the first and second housing members.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a needle stick protection device 10 is disclosed. The needle stick protection device 10 includes a housing 12 shaped and dimensioned for positioning about a needle 14 and an associated syringe 16. In accordance with a preferred embodiment, the needle stick protection device 10 is shaped and dimensioned to receive a 10 ml syringe with a 1.5" needle in place (for example, an INJECT10$^N$ needle). The housing 12 includes a first housing member 18 telescopically coupled to a second housing member 20. As will be appreciated based upon the following disclosure, the second housing member 20 is free to move relative to the first housing member 18 under the control of the locking assembly disclosed below. The first housing member 18 includes an open first end 22 and an open second end 24.

Figure 4:
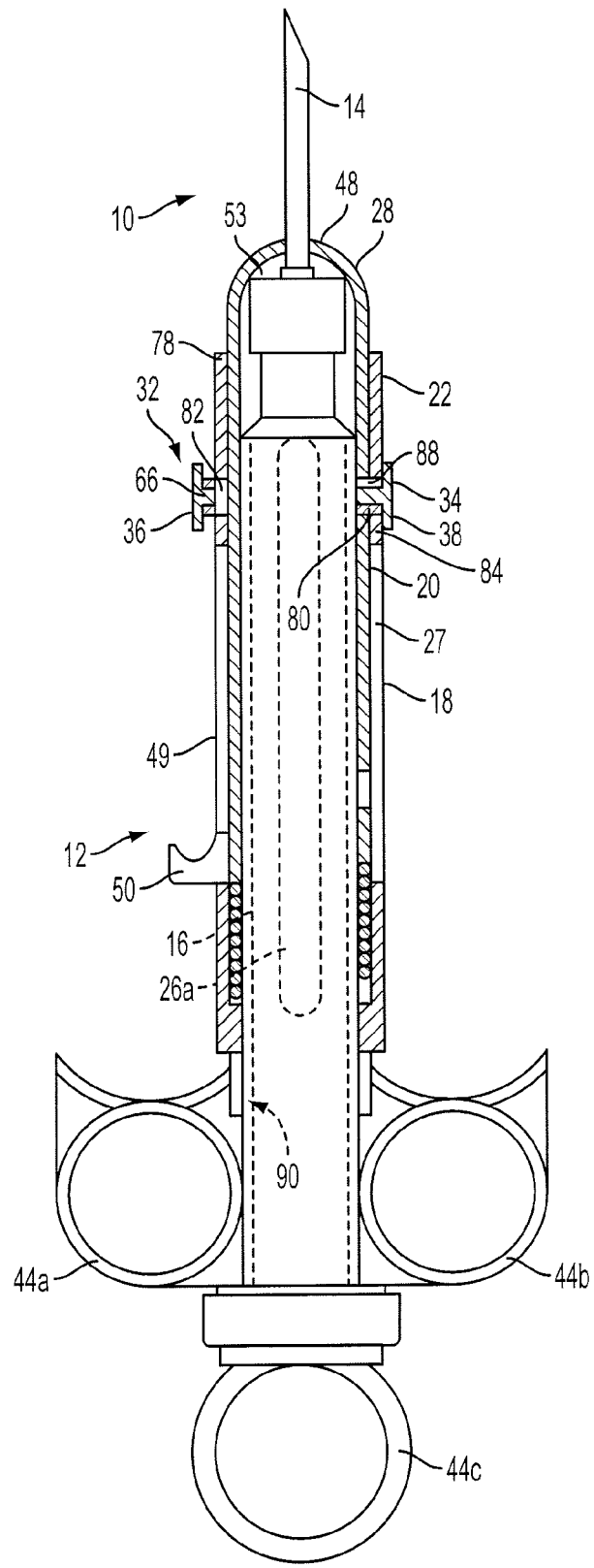
FIG. 4 is a side partial cross-sectional view of the present needle stick protection device in its retracted orientation.
Figure 5:
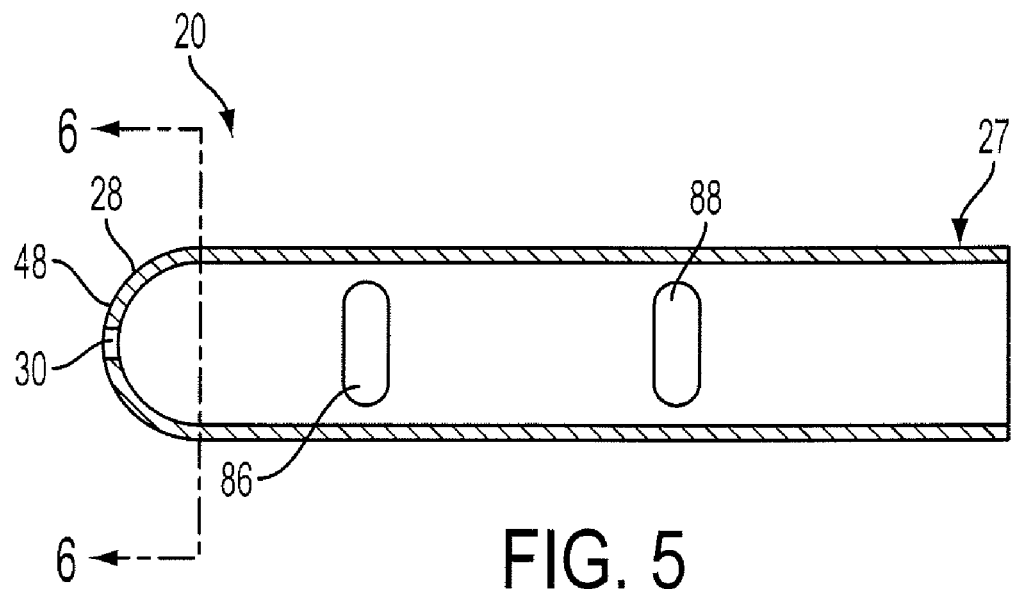
FIG. 5 is a cross sectional view of the second housing member.
Figure 6:
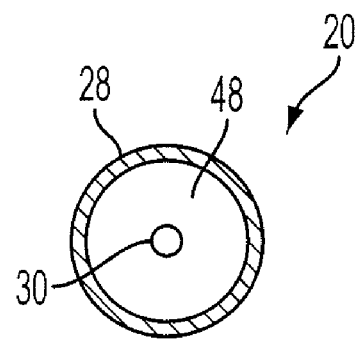
FIG. 6 is a cross sectional view along the line 6-6 in FIG. 5.
Figure 7:
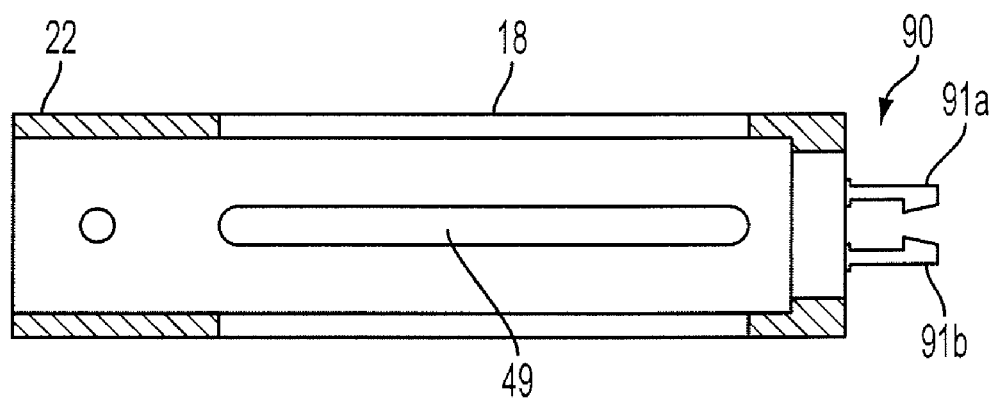
FIG. 7 is a cross sectional view along the line 7-7 of the first housing member.
Figure 8:
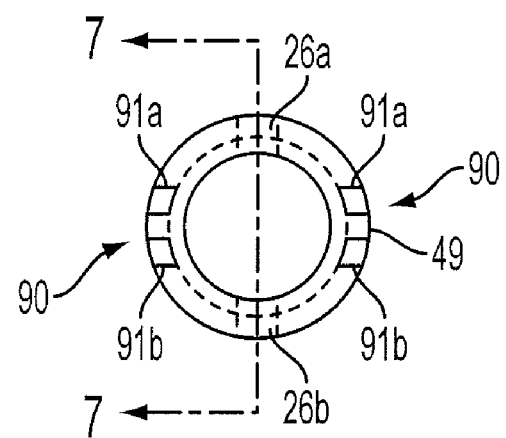
FIG. 8 is a cross sectional view along the line 8-8 in FIG. 7.
Figure 9:
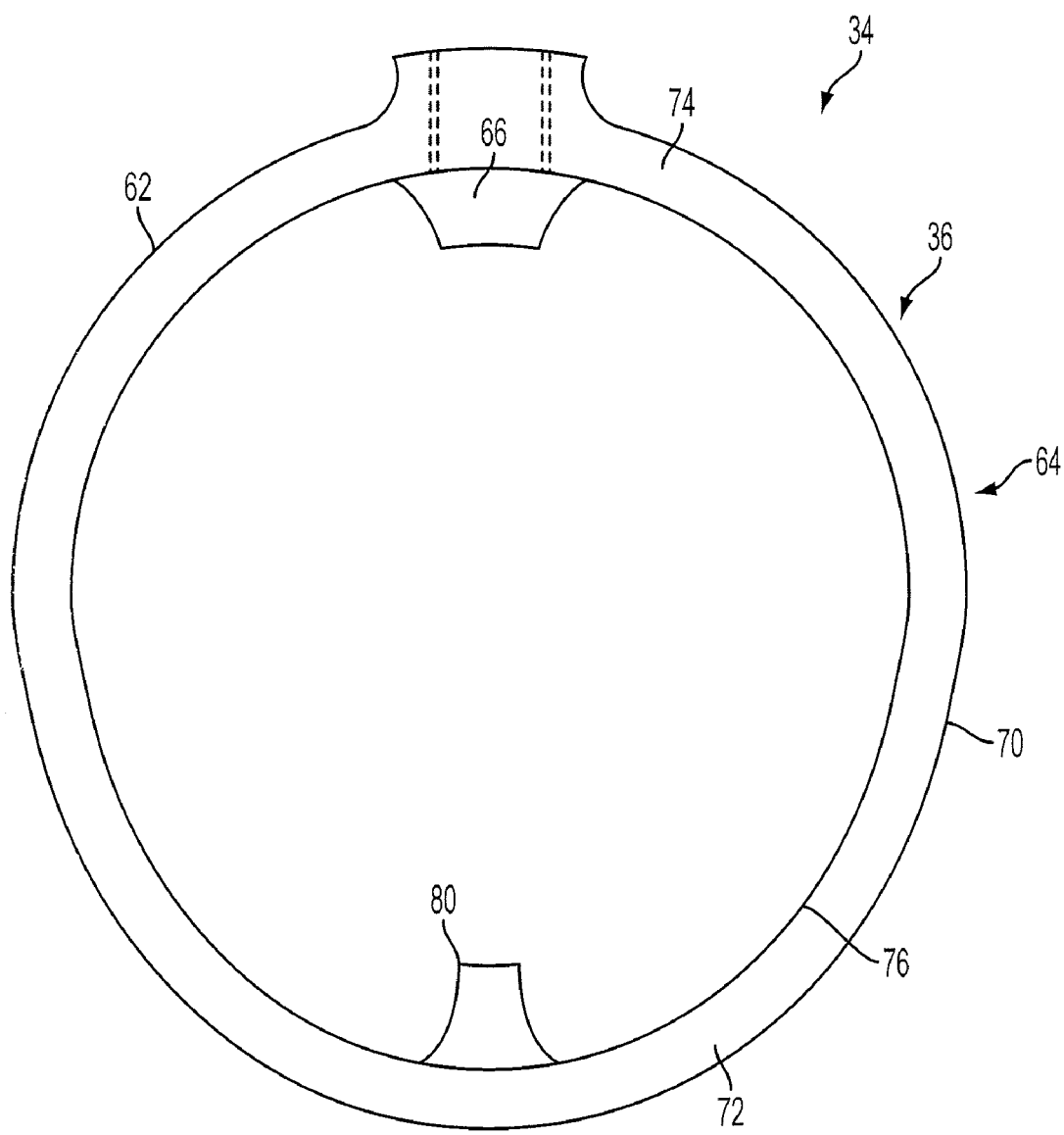
FIG. 9 is a side view of an alternate shield trigger in accordance with the present invention.

The first housing member 18 further includes viewing slots 26a, 26b extending longitudinally along the length of the first housing member 18 along opposite sides of the first housing member 18 allowing a medical practitioner to view the syringe 16 held within the housing 12. The first housing member 18 also includes a guide slot 49 to accommodate a slide actuating portion 50. The guide slot 49 is located at an angle of 90 degrees from slots 26a, 26b and extends from the location shown in FIGS. 1, 4 and 7 wherein the needle 14 is axially shielded and the spring 40 is fully cocked.

The second housing member 20 includes an open first end 27 and a substantially closed second end 28. The second end 28 includes an aperture 30 shaped and dimensioned to permit the passage of the needle 14 therethrough.

The needle stick protection device 10 also includes a locking assembly associated with each of the first housing member 18 and the second housing member 20 for controlling relative movement thereof.

The present needle stick protection device 10 provides a mechanism by which the needle 14 may be shielded and unshielded by the physician in a controlled manner and whenever so required by the physician. As such, this can be done repetitively as often as required by the physician during a medical procedure. The locking mechanism of the present needle stick protection device 10 also provides for permanent shielding of the needle 14 once a procedure is completed. As a result, once the needle 14 is permanently shielded in accordance with this embodiment, the needle stick protection device 10 is ready for disposal in a suitable container.

The construction of the present needle stick protection device 10 employs a distinctive locking assembly 32. In particular, the locking assembly 32 of the present needle stick protection device 10 includes a shield trigger 34 composed of a resilient first arcuate member 36 and a resilient second arcuate members 38 coupled at opposite ends for positioning about the first housing member 18. As will be appreciated based upon the following disclosure, the shield trigger 34 cannot be moved axially on first housing member 18. The shield trigger 34 is fixed in its location on the first housing member 18 by either short locator plug 66 or long locator plug 80 as discussed below in greater detail. Briefly, however, it will be appreciated, either short locator plug 66 or long locator plug 80 are located in their respective recesses and apertures, although short locator plug 66 and long locator plug 80 cannot be fully positioned in their respective recesses and apertures at the same time. As discussed below in describing operation of the present locking assembly 32, the first arcuate member 36 and the second arcuate member 38 are resilient to allow for bowing (that is, lateral bending along a plane parallel to the plane in which the arcuate member 38 lies) thereof upon the application of force in the practice of the present invention. However, each of the first arcuate member 36 and the second arcuate member 38 has a resting configuration when no force is being applied thereto.

The first arcuate member 36 includes a first end 62 and a second end 64. An inwardly directed short locator plug 66 is positioned centrally between the first end 62 and the second end 64 of the first arcuate member 36. The second arcuate member 38 includes a first end 68 and a second end 70. An inwardly directed long locator plug 80 is positioned centrally between the first end and the second end of the second arcuate member 38. The first ends of the respective first and second arcuate members 36, 38 are coupled and the second ends of the respective first and second arcuate members 36, 38 are coupled to form a complete circular member, that is, a locking ring 72, shaped and dimensioned to fit about the first housing member 18 for performance of the functions discussed below in greater detail.

The first arcuate member 36 covers an arc of less than 180 degrees, while the second arcuate member 38 covers an arc of more than 180 degrees. In addition, the concave inner surface 74 of the first arcuate member 36 has a resting radius of curvature (that is, when no force is applied to the first arcuate member) which is less than a resting radius of curvature (that is, when no force is applied to the second arcuate member) of the concave inner surface 76 of the second arcuate member 38. Further, and as will be appreciated based upon the following disclosure, the radius of curvature along the convex outer surface 78 of the first housing member 18 is substantially the same as the resting radius of the curvature along the concave inner surface 76 of the second arcuate member 38.

As a result of the relationship between the concave inner surface 74 of the first arcuate member 36, the concave inner surface 76 of the second arcuate member 38 and the convex outer surface 78 of the first housing member 18, the locking ring 72 is biased to a resting orientation with the concave inner surface 76 of the second arcuate member 38 conforming to the convex outer surface 78 of the first housing member 18 and the concave inner surface 74 of the first arcuate member 36 spaced from the convex outer surface 78 of the first housing member 18. In this orientation, which is the locked orientation, the inwardly directed long locator plug 80 extends through the wall of the first housing member 18 for engagement with the second housing member 20. As discussed above, when the locking ring 72 is in its locked orientation, the concave inner surface 74 of the first arcuate member 36 is spaced from the convex outer surface 78 of the first housing member 18. Consequently, the inwardly directed short locator plug 66 is spaced from a short plug aperture (or recess) 82 formed along the wall of the first housing member 18.

When one, however, presses with sufficient pressure upon the first arcuate member 36 and forces the concave inner surface 74 of the first arcuate member 36 toward the convex outer surface 78 of the first housing member 18, the bias generated by the interaction between the first arcuate member 36, the second arcuate member 38 and the convex outer surface 78 of the first housing member 18 is overcome. With this force, the locking ring 72 is moved to its release orientation. In its release orientation, the concave inner surface 74 of the first arcuate member 36 bends to substantially conform to the convex outer surface 78 of the first housing member 18 with the inwardly directed short locator plug 66 seated within a short plug aperture 82 formed in the wall of the first housing member 18 but not extending through the wall of the first housing member 18. The concave inner surface 76 of the second arcuate member 38 is moved from the convex outer surface 78 of the first housing member 18, and the inwardly directed long locator plug 80 is moved radially outwardly such that it moves from its interference positioned extending through the long plug aperture 84 in the first housing member 18 and the retracted recess 86 or the covered recess 88 of second housing member 18. However, the inwardly directed long locator plug 80 is of a length such that when it is in the release orientation, it radially moves from its position within the retracted recess 86 or the covered recess 88 within the wall of the second housing member 18 while still remaining in the long plug aperture 84 of the first housing member 18. As such, nothing interferes with the relative movement of the first housing member 18 and the second housing member 20 and they are free to move as desired by the physician, or other medical practitioner performing the medical procedure.

In use, the second housing member 20 moves relative to the first housing member 18 to facilitate retraction and extension of the needle 14 through the aperture 30 at the second end 28 of the second housing member 20. With this in mind, the second housing member 20 is hand biased relative to the first housing member 18 in a manner forcing the first end 27 of the second housing member 20 away from the first end 22 of the first housing member 18 to maintain the second housing member 20 in a covered position in which the needle 14 is fully contained within the housing 12; that is, the short and long locator plugs 66, 80 are selectively seated within the respective short plug aperture 82, long plug aperture 84, retracted recess 86 and the covered recess 88 formed along the outer walls of the first and second housing members 18, 20 to selectively maintain the second housing member 20 in its covered position.

The manually operated second housing member 20 is axially driven by a coil spring 40 relative to the first housing member 18 such that the second housing member 20 covers and uncovers the entire needle 14 with the spring 40 forcing the second housing member 20 to an uncovered orientation, that is, the spring 40 is biased to draw the second housing member 18 toward the first housing member 18 when the locking ring 72 is moved to its release orientation. However, the second housing member 20 is automatically locked in position relative to the first housing member 18 by the inherent bias of the locking ring 72 and consequently the bias forcing the short and long locator plugs 66, 80 to positions interfering with the relative movement of the first and second housing members 18, 20 so as to provide positive needle stick protection when the second housing member 20 is in its fully extended position.

The present needle stick protection device 10 is designed to work with a conventional three-finger syringe arrangement 44a-c commonly utilized within the industry and thereby provides the ability to push and pull on the syringe plunger 46. By using transparent plastic in the construction of the present needle stick protection device 10, the device 10 enables the physician to readily see the contents of the syringe 16. The needle stick protection device 10 is attached to the syringe 16 at the two-finger location so the needle stick protection device 10 cannot move axially with respect to the syringe. In accordance with a preferred embodiment of the present invention, the second end of the first housing member 18 is provided with latch members 90 that engages and retains the syringe in position relative to the first housing member 18 and the second housing member 20.

With regard to the housing 12, and in particular the second housing member 20, it is essentially a cylindrical tube which is open at the first end 27 and has a integral, hemispherical closure 48 at the second end 28 in a covered position in which the needle 14 is fully unshielded; that is, seating the short locator plug 66 in the short plug aperture 82 removes the long locator plug 80 from its covered recess 88 in the second housing member 20 so that the second housing member (or shield) 20 may be moved; that is, the slide actuating portion 50 may be moved so that first end 27 of the second housing member moves away from first end 22 of the first housing member resulting in the manually unshielding of the needle and cocking of the spring 40. In particular, the slide actuating portion 50 is a finger grip attached to the second housing member 20. The slide actuating portion 50 is used by the physician to a) uncover the needle and b) cock the spring 40 so the needle shielding may be achieved by merely actuating the shield trigger 34.

Movement of the slide actuating portion 50 (as well as the second housing member 20 relative to the first housing member 18 is facilitated by the provision of the guide slot 49 in the wall of the first housing member 18. The long plug 80 enters the long plug recess 86 when the spring 40 is fully cocked. The unshielded configuration (as shown with reference to FIG. 4) is maintained as long as the long plug 80 is seated in its retracted recess 86. The hemispherical closure 48 has a centrally located aperture 30 through which the needle 14 can freely pass as the second housing member 20 is moved axially to cover and uncover the needle 14. The open first end 27 of the second housing member 20 is fitted with slide actuating portion 50 for example, pins, cylindrical thumb pads, etc., which are used to manually retract the second housing member 20 so that it uncovers the entire needle 14. The manually operated second housing member 20 is axially driven by a coil spring 40 relative to the first housing member 18 such that the second housing member 20 covers the entire needle 14 when the spring 40 forces the second housing member 20 to an uncovered orientation, that is, the spring 40 is biased to force the second housing member 20 away from the first housing member 18 when the locking ring 72 is moved to its release orientation in which the long plug 80 is removed from its retracted recess 86 and seats in the covered recess 88. Due to the unsymmetrical geometry of the locking ring 72, the locking ring 72 is radially biased to force the long plug 80 into its retracted recess 86 or cover recess 88 to have the free end of the long plug 80 slide along the outer surface 78 of housing member 20 between retracted recess 86 and covered recess 88 of the long plug 80. In accordance with a preferred embodiment, the slide actuating portion 50 is a thumb pad which extends from the respective detents 31a, 31b passing through the slots 26a, 26b. The thumb pad 50 permits ready manipulation of the second housing member 20.

The second housing member 20 is locked in place, either in its extended position where the needle 14 is covered or in its retracted position where the needle 14 is uncovered, by the interaction of the inwardly directed long locator plug 80 with the covered recess 88 of the second housing member 20 and the retracted recess 86 of the second housing member 20. With this in mind, the covered recess 88 is located adjacent the first end 27 of the second housing member 18 and the retracted recess 86 is located adjacent the second end 28 of the second housing member 18. Assuming the second housing member 20 is in its retracted orientation with the inwardly directed long locator plug 80 seated within the retracted recess 86 of the second housing member 20, when the medical practitioner presses upon the locking ring 72 moving it to its release orientation, the inwardly directed long locator plug 80 moves from its position within the retracted recess 86 allowing relative movement between the first housing member 18 and the second housing member 20. In this released orientation, the coil spring 40 pushes the second housing member 20 relative to the first housing member 18 to axially cover the needle tip 53. The inherent bias of the locking ring 72 will force the inwardly directed long locator plug 80 toward the second housing member 20. However, because the second housing member 20 only includes the covered recess 88 and the retracted recess 86, with a smooth outer surface therebetween, the inwardly directed long locator plug 80 rides along the outer surface 78 of the second housing member 20 until the covered recess 88 aligns with the inwardly directed long locator plug 80 at which point the inwardly directed long locator plug 80 will seat therein due to the inherent bias of the locking ring 72. In particular, once the needle 14 is fully covered, the covered recess 88 aligns with the long plug aperture 84 of the first housing member 18 allowing the inwardly directed long locator plug 80 to seat within the covered recess 88 creating interference between the first and second housing members 18, 20 preventing further movement relative thereto.

In practice, and with reference to FIG. 1, the needle 14 is shown in its shielded configuration. The second housing member 20 is locked in place by long plug 80 seating within the covered recess 88 of the second housing member 20. The spring 40 is fully extended and unloaded when the first housing member 18 and second housing member 20 assume this orientation. The slide actuating portion 50, which is attached to second housing member 20, and the seating of the long locator plug 80 within the covered recess 88 stopped the axial travel of second housing member 20. The physician can then unlock the shield trigger 34 by pushing it radially so that short locator plug 66 enters the short plug aperture 82 in the first housing member 18 and the long plug 80 is pulled out of the covered recess 88 of the second housing member 20. This frees the second housing member 20 so that it can move axially and thereby uncover the needle 14. The physician then cocks the spring 40 by pushing the slide actuating portion 50 toward the finger grips 44a-c until the long locator plug 80 of the shield trigger 34 slips into the retracted recess 86 in second housing member 20. The needle 14 is now fully exposed and the second housing member 20 is locked in the needle exposed configuration. The spring 40 is cocked and ready to quickly shield the needle when the shield trigger 34 is actuated by pushing the short locator plug 66 into the short plug aperture 82 of the first housing member 18. As a result, when it is desired to move the second housing member 18 to its extracted position for use of the needle 14, when the medical practitioner presses upon the locking ring 72 moving it to its release orientation, the inwardly directed long locator plug 80 moves from its position within the covered recess 88 allowing relative movement between the first housing member 18 and the second housing member 20. In this released orientation, the medical practitioner uses the slide actuating portion 50 to expose the needle 14 and simultaneously cock the spring 40 by sliding slide actuating portion 50 toward the three finger portion 44a,b,c until the long locator plug 80 is seated in the retracted recess 86 in the second housing member 20. During movement in this manner, the practitioner may release the locking ring 72 and the inherent bias of the locking ring 72 will force the inwardly directed long locator plug 80 toward the second housing member 20. However, because the second housing member 20 only includes the covered recess 88 and the retracted recess 86, with a smooth outer surface therebetween, the inwardly directed long locator plug 80 rides along the outer surface 78 of the second housing member 20 until the retracted recess 86 aligns with the inwardly directed long locator plug 80 at which point the inwardly directed long locator plug 80 will seat therein due to the inherent bias of the locking ring 72. In particular, once the needle 14 is fully uncovered, the retracted recess 86 aligns with the long plug aperture 84 of the first housing member 18 allowing the inwardly directed long locator plug 80 to seat within the retracted recess 86 creating interference between the first and second housing members 18, 20 preventing further movement relative thereto.

The needle 14 is shielded by pushing radially on the shield trigger 34 so that the short locator plug 66 enters the short plug aperture 82 in the first housing member 18. This moves the long locator plug 80 out of its retracted recess 86 in second housing member 20 so that the spring 40 can quickly drive the second housing member 20 into its needle shielding and locked configuration (see FIG. 4). The entire procedure, that is, shielding and unshielding of the needle 14, may be repeated as many times as necessary during the surgical procedure.

As discussed above, the first housing member 18 is selectively coupled to the finger holes 44a and 44b via the latch members 90 and is thereby permanently secured to the syringe 16 so that it cannot be moved axially with respect to the syringe 16. Each of the latch members 90 is composed of resilient, facing latch arms 91a, 91b shaped to allow for the positioning of the respective finger holes 44a, 44b therebetween in a manner holding the syringe 16 in position relative to the first housing member 18. The first housing member 18 is also adapted to constrain the coil spring 40 used to extend the second housing member 20 when covering the needle 14 during the needle shielding process.

In accordance with preferred embodiments of the present invention, two design configurations are contemplated for use in conjunction with the helical compression spring 40. Mathematical analyses were conducted, and are available, in all critical design areas. For example, the geometry of the first arcuate member 34 and the second arcuate member of the shield trigger 34 was designed to produce a restoring force on the long plug 80 which would automatically lock the second housing member 20 in place in the selected configuration, that is, needle shielded or unshielded, when the shield trigger 34 was released. Further, the analysis may be used to calculate the angular arc lengths, radii, etc. of the shield trigger 34 which will ensure that the finger forces required and the stresses developed in the shield trigger 34 are acceptable. Specifically, and in accordance with preferred embodiments of the present invention, the following criteria are contemplated for use as the spring 40 in order to provide an alternate spring rate choice for the physician:

|  | Spring 1 | Spring 2 |
|---|---|---|
| Wire Gage | 18 Ga | 17 Ga |
| Wire Diameter | 0.047" | 0.054" |
| Mean Coil Diameter | 0.827" | 0.802" |
| Coil Pitch | 0.151" | 0.14" |
| Number of Active Cells | 15 | 16 |
| Unloaded Spring Length | 2½" | 2½" |
| Spring Rate | 0.82#/in. | 1.45#/in. |
| Loaded Deflection | 1½" | 1½" |
| Spring OD When Compressed to Solid | 0.877" | 0.860" |
| Solid height for springs with ground ends | 0.783" | 0.964" |
| Solid height for springs with unground ends | 0.830" | 1.018" |

In use, the present needle stick protection device 10 can be completely assembled and will function with or without the syringe 16 in place. The entire syringe 16 with the needle 14 attached is placed in the needle stick protection device 10 and is locked in the first housing member 18. The physician can then expose the needle 14 as described above, insert the needle 14 into the patient as many times as necessary, shielding and unshielding the needle 14 each time it is transferred back and forth between the physician and the medical technician. As mentioned above, since the needle stick protection device is made of transparent plastics, the physician can readily determine when the needle is in a blood vessel by slightly withdrawing the syringe plunger.

When it is desired to dispose of the needle 14 and the needle stick protection device 10 a drop of fast acting cement may be applied to the portion of the shield trigger 34 in contact with the first housing member 18 so that the shield trigger 34 cannot be actuated. This will lock the second housing member 20 in its needle shielded configuration so that the entire device 10 may be disposed of safely.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A needle stick protection device, comprising:
a housing shaped and dimensioned for positioning about a syringe including a needle extending therefrom, the housing includes a first housing member telescopically coupled to a second housing member;
the first housing member includes a first end shaped and dimensioned for receiving the syringe and a second end;
the second housing member includes a first end and a substantially closed second end, the second end includes an aperture shaped and dimensioned to permit the passage of the needle therethrough;
a locking assembly is associated with the first housing member and the second housing member for selectively controlling movement of the first housing member relative to the second housing member, the locking assembly includes a resilient first arcuate member and a resilient second arcuate member coupled at opposite ends thereof to define a locking ring shaped and dimensioned for positioning about the first housing member;
the first arcuate member includes a concave inner surface;
the second arcuate member includes a concave inner surface from which an inwardly directed long locator plug;
wherein the locking ring moves between a locked orientation with the inwardly directed long locator plug preventing relative movement between the first housing member and the second housing member and a release orientation with the inwardly directed long locator plug moved from its interference position preventing relative movement between the first housing member and the second housing member.

2. The needle stick protection device according to claim 1, wherein the first arcuate member covers an arc of less than 180 degrees and the second arcuate member covers an arc of more than 180 degrees.

3. The needle stick protection device according to claim 2, wherein the concave inner surface of the first arcuate member has a resting radius of curvature which is less than a resting radius of curvature of the concave inner surface of the second arcuate member.

4. The needle stick protection device according to claim 3, wherein a radius of curvature along a convex outer surface of the first housing member is substantially the same as the resting radius of the curvature along the concave inner surface of the second arcuate member.

5. The needle stick protection device according to claim 4, wherein the locking ring is biased to a resting orientation with the concave inner surface of the second arcuate member conforming to the convex outer surface of the first housing member and the concave inner surface of the first arcuate member spaced from the convex outer surface of the first housing member.

6. The needle stick protection device according to claim 1, wherein the concave inner surface of the first arcuate member has a resting radius of curvature which is less than a resting radius of curvature of the concave inner surface of the second arcuate member.

7. The needle stick protection device according to claim 6, wherein a radius of curvature along a convex outer surface of the first housing member is substantially the same as the resting radius of the curvature along the concave inner surface of the second arcuate member.

8. The needle stick protection device according to claim 7, wherein the locking ring is biased to a resting orientation with the concave inner surface of the second arcuate member conforming to the convex outer surface of the first housing member and the concave inner surface of the first arcuate member spaced from the convex outer surface of the first housing member, however, when one presses with sufficient pressure upon the first arcuate member and forces the concave inner surface of the first arcuate member toward the convex outer surface of the first housing member, the bias generated by the interaction between the first arcuate member, the second arcuate member and the convex outer surface of the first housing member is overcome and the locking ring is moved to its release orientation.

9. The needle stick protection device according to claim 8, wherein the resting orientation is a locked orientation and wherein the inwardly directed long locator plug extends through a wall of the first housing member for engagement with the second housing member.

10. The needle stick protection device according to claim 9, wherein the first arcuate member includes an inwardly directed short locator plug extending from the concave inner surface of the first arcuate member and the inwardly directed short locator plug is spaced from the wall of the first housing member when the locking ring is in its locked orientation.

11. The needle stick protection device according to claim 10, wherein the locking ring, when in its release orientation, has the concave inner surface of the first arcuate member bent to substantially conform to the convex outer surface of the first housing member with the inwardly directed short locator plug seated within a short plug aperture formed in the wall of the first housing member but not extending through the wall of the first housing member, and the concave inner surface of the second arcuate member is moved from the convex outer surface of the first housing member, and the inwardly directed long locator plug is moved radially outwardly such that it moves from its interference position extending through the long plug aperture in the first housing member and a retracted recess or a covered recess of the second housing member.

12. The needle stick protection device according to claim 9, wherein the locking ring, when in its release orientation, has the concave inner surface of the first arcuate member bent to substantially conform to the convex outer surface of the first housing member, and the concave inner surface of the second arcuate member is moved from the convex outer surface of the first housing member, and the inwardly directed long locator plug is moved radially outwardly such that it moves from its interference position extending through the long plug aperture in the first housing member and a retracted recess or a covered recess of the second housing member.

* * * * *